United States Patent [19]

Allison et al.

[11] 4,053,585

[45] Oct. 11, 1977

[54] IMMUNOLOGICAL PREPARATIONS

[75] Inventors: Anthony Clifford Allison, London; Gregory Gregoriadis, Kenton, both of England

[73] Assignee: National Research Development Corporation, England

[21] Appl. No.: 590,270

[22] Filed: June 25, 1975

[30] Foreign Application Priority Data

June 25, 1974 United Kingdom ............... 28131/74

[51] Int. Cl.² ..................... A61K 39/00; A61K 39/02; A61K 39/12; A61K 39/18
[52] U.S. Cl. ....................................... 424/92; 424/88; 424/89; 424/199
[58] Field of Search .................................. 424/88-92, 424/199

[56] References Cited

U.S. PATENT DOCUMENTS

| | | | |
|---|---|---|---|
| 3,317,393 | 5/1967 | Chanock et al. | 424/89 |
| 3,376,199 | 4/1968 | Colbs et al. | 424/89 |
| 3,384,544 | 5/1968 | Walton et al. | 424/92 |
| 3,492,399 | 1/1970 | Prigal | 424/91 |
| 3,579,633 | 5/1971 | Thomson | 424/92 |
| 3,594,476 | 7/1971 | Merrill | 424/199 |
| 3,608,066 | 9/1971 | Illartein | 424/46 |
| 3,715,432 | 2/1973 | Merrill | 424/199 |
| 3,752,886 | 8/1973 | Munder et al. | 424/199 |
| 3,755,557 | 8/1973 | Jacobs | 424/46 |
| 3,887,698 | 6/1975 | McConnell et al. | 424/12 |

FOREIGN PATENT DOCUMENTS 2,249,552   5/1973   Germany

OTHER PUBLICATIONS

Chem. Abst. 79 No. 45830T of Ger. Offen. 2,249,552 May 30, 1973.
Chem. Abst. 81 No. 82398V of S. Afr. 73 01,850 Nov. 14, 1973.
Chem. Abst. 83 No. 33053M of Neth. Appl. 74 04,133 Sept. 25, 1974.
Chem. Abst. 83 No. 33033E of Fr. Demande 2,221,122 Oct. 11, 1974.
Chem. Abst. 83 No. 229V of Juliano et al., Biochem. BioPhys. Res. Commun. 1975 63(3), pp. 651-658, Effect of Particle Size and Charge on the Clearance Rates of Liposomes and Liposome Encapsulated Drugs.
7,301,850 11001973 ZA
Mellanby et al. (1968) J. Gen. Microbiol. 54: pp. 161-168 "Ganglioside as a Prophylactic Agent in Experimental Tetanus in Mice".
Sessa et al. J. Biol. Chem. (1970) 245(13): pp. 3295-3301 "Incorporation of Lysozyme into Liposomes."
Kaplan (1972) Biochem. Biophys. Acta 290: pp. 339-347 "Anion Diffusion across Artificial Lipid Membranes."
Papahadjopoulos et al. Biochem. Biophys. ACTA. 352:10-28 May 30, 1974 "Membrane Fusion and Molecular Segregation in Phospholipid Vesicles."
Juliano et al. Biochem. Biophys. Res. Comm. 63(3) (1975) pp. 651-658 "The Effect of Particle Size and Charge on the Clearance Rates of Liposomes and Liposome Encapsulated Drugs."

Primary Examiner—Shep K. Rose
Attorney, Agent, or Firm—Jacobs & Jacobs

[57] ABSTRACT

Immunological preparations are described in which liposomes having a negative charge are used as adjuvants for the purposes of human and veterinary vaccines containing viral or bacterial antigens. The formulation of influenza antigen, and diphtheria and tetanus toxoid antigens in liposomes formed with egg lecithin is described and the adjuvant effect demonstrated.

16 Claims, No Drawings

IMMUNOLOGICAL PREPARATIONS

This invention relates to immunological preparations including antigenic compositions e.g. viral and bacterial vaccines and antibody preparations, and is more particularly concerned with immunological preparations containing adjuvants.

Adjuvants are substances that enhance the immune response of a specific antigen. Examples of adjuvants are Freund's incomplete adjuvant, a water-in-oil emulsion containing the antigen, and Freund's complete adjuvant, which is the same with killed tubercle bacilli. Unfortunately, the mineral oils currently available for use as adjuvants are not readily degraded in man and persist at the injection site thereby causing unacceptable granulomas or other undesirable effects. There is however a real need for a safe and effective adjuvant for use in human immunization programmes. Such an adjuvant could reduce the amounts of antigens, e.g. diptheria and tetanus toxoids, required for protective immunization, with corresponding economies especially relevant to the developing countries. The need for improved adjuvants in veterinary vaccines also exists.

Furthermore, it is desirable to administer as many vaccines as possible at the same time, so that one or a few injections can immunize humans or animals against a wide range of organisms or their toxic products. This is especially relevant to tropical countries where, in addition to the infections of temperate climates, there is exposure to many parasitic infections. When two or more antigens are administered simultaneously, each may reduce the formation of antibodies against the other, by a phenomenon known as antigenic competition. In addition the choice of suitable adjuvant materials is also controlled by the need to avoid allergic reactions.

It has now been found that preparations based on lipids when in the form of "liposomes" (as defined hereinafter), are excellent in many respects as adjuvants provided the surface of the liposome carries a negative charge. Adjuvant preparations based on negatively charged liposomes elicit the formation of much higher concentrations of antibodies than are elicited by the use of free antigen. On the other hand, antigens entrapped in positively charged liposomes elicit less antibody than the same dose of the free antigen. Although liposomes have been proposed in a number of publications for the entrapment of drugs and other substances, their previous use in the formation of immunologically effective preparations has not been proposed. Indeed, the mechanism by which liposomes containing other active materials are believed to act in vivo would be considered contra-indicative of their use in connection with antigenic and like materials.

Accordingly the present invention comprises immunlogically active preparations in which the desired immunlogically effective agent is incorporated in liposomes having a negative charge.

Liposomes have been described in the literature (Biochemical Journal, 1972, 129, 123; Nature, 1973, 244, 170; New Scientist, 1973, 890; FEBS Letters, 1973, 36, 292; Biochemical Journal, 1974, 140, 323) and their general structure is well known to biological research workers. Liposomes are onion-like structures comprising a series of lipid layers spaced one from another by aqueous material, the outermost layer being lipid. When used in accordance with the invention, aqueous layers located between lipid layers contain a dissolved or dispersed immunologically effective agent. A broad variety of lipid maerials may be used to form liposomes. Preferred lipids are those which are non-immunogenic and biodegradable, notably the phospholipids such as natural lecithins e.g. egg lecithin, or synthetic lecithins e.g. dipalmitoyl lecithin. Such materials fulfill the requirements indicated above and possess certain additional advantages. Since the active material is entrapped within the liposome structure, higher doses can be given than with the free antigen. Furthermore, the immunological agent is retained within the liposome structure until it reaches the site of action and therefore allergic reactions are considerably reduced.

Liposomes also facilitate the use of multiple antigens including those which should be maintained out of contact with one another at least for a time. Competitive antigens can be incorporated in different populations of liposomes carrying different components, and mixtures of these can be administered together. The adjuvant effect of compositions in accordance with the invention may be further enhanced by incorporating other materials which have adjuvant activity into the liposome e.g. saponins.

Liposomes are versatile carriers for antigens, adjuvants or other biologically active compounds. They have both aqueous and lipid compartments, and substances of very high molecular weight can be incorporated into them. Compounds of molecular weight up to about 300,000 daltons can be entrapped in smaller liposomes and the larger multilamellar liposomes can be used for molecular weights of 500,000 and above. The chemical composition of the liposomes, and with it properties such as charge, can be varied over a wide range, and materials can be attached to the surface of liposomes as well as incorporated within them. As indicted above, the adjuvant effect is achieved only with liposomes which are negatively charged. A suitably charged liposome surface can be achieved in the course of preparing the liposome, for example, with the use of added acidic substances.

In the preparation of preferred liposome structures in accordance with the invention it is customary to use a phospholipid such as egg lecithin as the main liposome-former. In addition other lipids e.g. cholesterol may be used in somewhat smaller proportions as a membrane strengthener. A third component will be the substance which is responsible for the negatively charged liposome surface, e.g., phosphatidic acid, dicetyl phosphate or beef brain ganglioside. These components may be present in the ratio, for example, of lecithin (7 moles), cholesterol (2 moles) and phosphatidic acid or equivalent (1 mole). Other substances may be incorporated into the structure for various purposes.

The invention will now be further described by means of specific Examples:

EXAMPLE 1

Egg lecithin (30 mg), cholesterol (4.4 mg) and phosphatidic acid (4.24 mg) are dissolved (3–4 ml) in a 50 ml spherical flask and evaporated under vacuum at 37° C. The thin lipid layer on the walls of the flask is then dispersed with 2 ml of diphtheria toxoid (12 mg/ml) as supplied by Wellcome Laboratories and after iodination with the iodine monochloride method. The suspension is allowed to stand at room temperature for about 2 hours during which time the liposomes form and mature. The suspension is then sonicated for 10 seconds.

Several hours later the suspension is passed through a Sepharose (6B column to separate the liposome-entrapped diphtheria toxoid. The liposomal preparation contains in a volume of about 4 ml 50% of the starting protein. The results of biological tests with the antigenic preparations so formed are given in Tables I, II and III.

Table I.

Serum antibody responses of mice to diphtheria toxoid (DT) administered intravenously as the free protein or entrapped in negatively charged liposomes

| Protein | Antibody concentration |
|---|---|
| Free | 1.8 |
| Liposomes | 10.0 |

240 $\mu g$ DT administered to groups of 15 TO mice, which were bled 14 days later.

Table II.

Serum antibody responses of mice to diphtheria toxoid (DT) administered subcutaneously as the free protein or entrapped in liposomes with positive or negative charges

| Mode of antigen administration | Antibody concentration |
|---|---|
| Primary responses | |
| a Free | 2.5 |
| b Negative liposomes | 6.7 |
| c Positive liposomes | 0 |
| Secondary responses | |
| d Free | 11.6 |
| e Negative liposomes | 13.3 |
| f Positive liposomes | 11.3 |

60 $\mu g$ DT free or entrapped in liposomes injected into the foot-pads of CBA mice, 6 per group. Primary responses wre measured after 14 days, booster injections of 20 $\mu g$ DT were given and the animals were bled 10 days later to measure secondary responses.

Table III.

Arthus reactions in immune mice challenged by injection into the footpad of 10 $\mu g$ diphtheria toxoid (DT) free or entrapped in negatively charged liposomes

| No. of mice | Challenge | Mean ratio of footpad thickness | Range |
|---|---|---|---|
| 10 | Free DT | 1.42 | 1.05–1.83 |
| 8 | Liposome-entrapped DT | 1.07 | 1.00–1.15 |

EXAMPLE 2

The procedure of Example 1 is followed for the preparation of liposome entrapped diphtheria toxoid (DT) with the exception that the equivalent amount of dicetyl phosphate (DP) (molecular weight 546, 3.1 mg) is used in place of phosphatidic acid. Groups of five BSVS/NIMR mie are injected intramuscularly with various amounts of diphtheria toxoid both liposome entrapped and as the free protein. After 14 days the mice are bled and primary antibody responses are measured by the indirect haemagglutination method (IHA) of Faulk and Houba (the Journal of Immunological Methods Volume 3 (1973) at pages 87–98). After bleeding the groups of mice are re-innoculated with the same amounts of antigens as initially, and after a further 13 days bled again, the secondary antibody responses being determined by the indirect haemagglutination method as above the results obtained are given in Table IV, the antibody responses expressed as the $\log_2$IHA titre.

Table IV

Effect of liposome (DP) entrapment on the immune responses to varying doses of diphtheria toxoid (DT)

| Dose of Antigen | Mode of Administration | Primary response (IHA) | Secondary response (IHA) |
|---|---|---|---|
| 1 $\mu g$ | Free | 0 | 0 |
| | Liposomes (DP) | 0 | 8.8 |
| 10 $\mu g$ | Free | 0 | 9.3 |
| | Liposomes (DP) | 2.3 | 10.3 |
| 60 $\mu g$ | Free | 7.0 | 10.7 |
| | Liposomes (DP) | 8.3 | 16.3 |

EXAMPLE 3

Liposome entrapped toxoid is prepared as in Example 2, and the effect upon antibody response of admixing killed *Mycobacterium tuberculosis* (BCG) organisms with the diphtheria toxoid is investigated. Separate groups of five BSVS/NIMR mice are injected with 20 $\mu g$ aliquots of diphtheria toxoid, free or liposome entrapped, both with and without admixture with heat killed *mycobacterium tuberculosis* (BCG) organisms. The mice are bled after 14 days and the primary antibody response (IHA) determined as in Example 2. Each group of mice is then re-inoculated with a further 20 $\mu g$ of diphtheria toxoid, presented in the same manner as in the initial inoculation but without BCG. After a further 10 days the mice are bled again and the secondary antibody response (IHA) is determined as above. The results obtained are given in Table V, the antibody responses expressed as in Example 2.

Table V

Effect of Liposome (DP) Entrapment of Diphtheria Toxoid with and without BCG on Primary and Secondary Responses

| Mode of Antigen administration | Primary Response (IHA) | Secondary Response (IHA) |
|---|---|---|
| Free | 0 | 12.6 |
| Free + BCG | 0 | 14.4 |
| Liposomes (DP) | 1.4 | 12.8 |
| Liposomes (DP) + BCG | 7.2 $p<0.01$ | 17.4 |

EXAMPLE 4

Similarly as for Example 3 the effect upon antibody responses of the admixture of *Bordetella pertussis* (BP) organisms with diptheria toxoid (DT) is investigated. Separate groups of five VSBS/NIMR mice are inoculated intramuscularly with 30 $\mu g$ of diphtheria toxoid (DT) as the free protein and also in liposome entrapped form, and in each case both with and without admixture of *Bordetella pertussis* (BP) organisms. The primary and secondary antibody responses are determined as in Example 2, the mice being bled after 14days, re-inoculated with a further 20 $\mu g$ of diphtheria toxoid, and bled again after a further 13days. The results obtained are given in Table VI.

Table VI

Effect of Liposome Entrapment of Diphtheria Toxoid with or without Bordetella pertussis (BP) organisms on primary and secondary antibody responses

| Mode of Antigen administration | Primary response (IHA) | Probability | Secondary response (IHA) |
|---|---|---|---|
| Free | 8.0 | | 12.0 |
| Free + BP | 10.2 | p 0.01 | 15.4 |
| Liposomes (DP) | 10.0 | p 0.01 | 15.6 |
| Liposomes (DP) + BP | 11.5 | p 0.01 | 19.7 |

EXAMPLE 5

Similarly as for Examples 3 and 4 the effect of saponin upon the immune response to liposome entrapped diphtheria toxoid (DT) is investigated. Groups of 5 adult VSVS/NIMR mice are injectd intramuscularly with 20 μg of free or liposome-entrapped diphtheria toxoid both with and without saponin. Two different levels of saponin admixture are investigated (3 μg and 50 μg). The primary and secondary antibody responses (IHA) are determined as in Example 3 the groups of mice being bled after 14 days, re-inoculated with the same antigens and bled again after a further 11 days. The results obtained are given in Table VII. Secondary challenge is made without saponin.

Table VII

| Effect of saponin on immune responses to liposome-entrapped diphtheria toxoid | | |
|---|---|---|
| Mode of antigen administration | Primary response (IHA) | Secondary Response (IHA) |
| Free | 0 | 5.4 |
| Liposomes (DP) | 0 | 7.5 |
| Liposomes (DP) + 3 μg saponin | 0 | 6.5 |
| Liposomes (DP) + 50 μg saponin | 0 | 12.6 |

EXAMPLE 6

Liposome entrapped tetanus toxoid (TT) is prepared by the method for the liposome entrapment of diphtheria toxoid, as described in Example 1, with the exception that the equivalent amount (3.1 mg) of dicetyl phosphate (DP) is used in place of phosphatidic acid (PA) and the antigenic component is tetanus toxoid (TT). The lipid layer is dispersed with 1.8 ml of iodinated tetanus toxoid (40Lf/ml Wellcome Laboratory). In other respects the method is the same as that used in Example 1 except that sonication was continued for 1 minute. Also by a similar method positively charged liposomes containing tetanus toxoid are prepared using the equivalent amount of stearylamine in place of dicetyl phosphate as above.

Groups of five adult VSBS/NIMR mice are injected intramuscularly with one Lf of tetanus toxoid in free form or entrapped in both positively and negatively charged liposomes. The primary and secondary antibody responses are determined by the indirect haemagglutination (IHA) method as in previous examples, the mice being bled 17 days after inoculation, re-inoculated with the same dose of antigen and bled again 10 days later. The results obtained are given in Table VIII.

Table VIII

| Effect of liposome entrapment on the immune response to tetanus toxoid | | |
|---|---|---|
| Mode of antigen administration | Primary response (IHA) | Secondary response (IHA) |
| Free | 1.2 | 14.4 |
| + Liposomes | 1.6 | 13.0 |
| − Liposomes (DP) | 4.4 | 17.6 |

EXAMPLE 7

In a further example the effect of liposome entrapment on the immune response of guinea pigs to detergent-extracted influenza virus haemagglutinin and neuraminidase is investigated. Liposome entrapped influenza virus haemagglutinin and neuraminidase is prepared essentially by the method for the preparation of liposome-entrapped diphtheria toxoid (DT) described in Example 1. Similarly as for Example 2, the equivalent amount of dicetyl phosphate is used in place of phosphatidic acid.

Two groups of five guinea pigs are inoculated intramuscularly with A/Port Chalmers vaccine, one group with the vaccine in the free form and the other with it liposome entrapped. The guinea pigs are bled after 20 days, re-inoculated with the same dose of virus and bled again after a further 12 days. The sera are assayed by radial diffusion and the primary and secondary antibody responses determined. The results obtained are given in Table IX.

Table IX

| Effect of liposome entrapment on the immune response of guinea pigs to detergent-extracted influenza virus haemagglutinin and neuraminidase | | |
|---|---|---|
| Mode of antigen administration | Primary response | Secondary response |
| Free | 0 | 9.7 |
| Liposomes (DP) | 0 | 13.5 |

EXAMPLE 8

The procedure of Example 7 is repeated but with the addition of saponin (50 μg).

We claim:

1. A pharmaceutical preparation for administration in vivo to effect immunization comprising an immunologically effective agent selected from bacterial toxoids which agent is incorporated essentially entrapped liposomes, said liposomes having a negative charge.

2. A pharmaceutical preparation according to claim 1, formulated as dosage units for use in humans.

3. A pharmaceutical preparation according to claim 1, wherein the agent is diphtheria toxoid.

4. A pharmaceutical preparation according to claim 1, wherein the agent is tetanus toxoid.

5. A pharmaceutical preparation according to claim 1, wherein the liposomes are formed with egg lecithin.

6. A pharmaceutical preparation according to claim 1, in which the negative charge is due to the presence of a substance selected from phosphatidic acid, dicetyl phosphate and beef brain ganglioside.

7. A method for the immunization of humans and animals against bacterial infections which comprises administering to such humans and animals an immunologically effective agent selected from bacterial toxoids which agent is incorporated essentially entrapped in liposomes, said liposomes having a negative charge.

8. A method according to claim 7, which comprises administering said immunologically effective agent to a human in unit dosage form.

9. A method according to claim 7, wherein the bacterial toxoid is diphtheria toxoid.

10. A method according to claim 7, wherein the bacterial toxoid is tetanus toxoid.

11. A method according to claim 7, wherein the immunologically effective agent is administered by injection.

12. A pharmaceutical method which comprises mixing a bacterial toxoid with a lipid and a substance capable of imparting a negative charge, sonicating this mixture to produce liposomes having a negative charge with which said bacterial toxoid is incorporated essentially entrapped, and administering said liposomes to a human or animal to effect immunization thereof.

13. A method according to claim 12, wherein the lipid is egg lecithin.

14. A method according to claim 12, wherein the substance capable of imparting a negative charge is selected from phosphatidic acid, dicetyl phosphate and beef brain ganglioside.

15. In the art of parenterally administering bacterial toxoids to patients susceptible to immunization therewith, the improvement which comprises administering such toxoids entrapped essentially in negatively charged liposomes to enhance the immune response thereto.

16. The improvement of claim 15, wherein the bacterial toxoid is diphtheria toxoid administered.

* * * * *